(12) United States Patent
Anderson et al.

(10) Patent No.: US 11,730,838 B2
(45) Date of Patent: *Aug. 22, 2023

(54) INACTIVATION OF GRAM-POSITIVE BACTERIA

(71) Applicant: University of Strathclyde, Glasgow (GB)

(72) Inventors: John Galloway Anderson, East Kilbride (GB); Michelle Maclean, Glasgow (GB); Gerald Alexander Woolsey, Queensland (AU); Scott John MacGregor, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 132 days.

This patent is subject to a terminal disclaimer.

(21) Appl. No.: 17/178,155

(22) Filed: Feb. 17, 2021

(65) Prior Publication Data

US 2021/0236670 A1 Aug. 5, 2021

Related U.S. Application Data

(63) Continuation of application No. 15/807,488, filed on Nov. 8, 2017, now Pat. No. 10,953,117, which is a continuation of application No. 14/657,398, filed on Mar. 13, 2015, now Pat. No. 9,839,706, which is a continuation of application No. 11/997,227, filed as (Continued)

(30) Foreign Application Priority Data

Jul. 29, 2005 (GB) .................................. 0515550

(51) Int. Cl.
*A61L 9/18* (2006.01)
*A61L 2/08* (2006.01)
*A61N 5/06* (2006.01)
*A61L 2/00* (2006.01)

(52) U.S. Cl.
CPC ................. *A61L 2/084* (2013.01); *A61L 9/18* (2013.01); *A61N 5/06* (2013.01); *A61L 2/0052* (2013.01)

(58) Field of Classification Search
CPC .................................. A61L 9/18; A61L 2/084
See application file for complete search history.

(56) References Cited

U.S. PATENT DOCUMENTS 3,926,556 A 12/1975 Boucher
3,992,646 A 11/1976 Corth
(Continued)

FOREIGN PATENT DOCUMENTS

AU 2006273860 B2 4/2012
CA 2617205 A1 2/2007
(Continued)

OTHER PUBLICATIONS

Additional excerpts from File History for U.S. Appl. No. 11/997,227, 17 pages.
(Continued)

*Primary Examiner* — Kevin Joyner
(74) *Attorney, Agent, or Firm* — Alston & Bird LLP

(57) ABSTRACT

A method for inactivating medically important Gram-positive bacteria including Methicillin-resistant *Staphylococcus aureus* (MRSA), Coagulase-Negative *Staphylococcus* (CONS), *Streptococcus, Enterococcus* and *Clostridium* species, comprising exposure to visible light, and in particular light within the wavelength range 400-500 nm.

7 Claims, 16 Drawing Sheets

Related U.S. Application Data application No. PCT/GB2006/002841 on Jul. 28, 2006, now Pat. No. 9,039,966.

(56) References Cited

U.S. PATENT DOCUMENTS

| | | | |
|---|---|---|---|
| D243,549 S | 3/1977 | Neveux | |
| 4,910,942 A | 3/1990 | Dunn et al. | |
| D350,212 S | 8/1994 | Yuen | |
| D351,248 S | 10/1994 | Yuen | |
| D380,845 S | 7/1997 | Chan | |
| D397,469 S | 8/1998 | Yumita et al. | |
| D407,519 S | 3/1999 | Chen | |
| 6,034,267 A | 3/2000 | Gierskcky et al. | |
| 6,251,127 B1 | 6/2001 | Biel | |
| 6,258,577 B1 | 7/2001 | Goodrich, Jr. et al. | |
| 6,627,730 B1 | 9/2003 | Burnie | |
| 6,875,225 B1 | 4/2005 | Pederson et al. | |
| D509,013 S | 8/2005 | Opolka | |
| D555,272 S | 11/2007 | Iai et al. | |
| D555,274 S | 11/2007 | Iai et al. | |
| 8,398,264 B2 | 3/2013 | Anderson | |
| 9,039,966 B2 | 5/2015 | Anderson et al. | |
| 9,839,706 B2 | 12/2017 | Anderson et al. | |
| 10,953,117 B2 | 3/2021 | Anderson et al. | |
| 2003/0023284 A1 | 1/2003 | Gartstein et al. | |
| 2003/0124023 A1 | 7/2003 | Burgess et al. | |
| 2004/0008523 A1 | 1/2004 | Butler | |
| 2004/0039242 A1 | 2/2004 | Tolkoff et al. | |
| 2004/0068305 A1 | 4/2004 | Bansal et al. | |
| 2004/0147984 A1 | 7/2004 | Altshuler et al. | |
| 2004/0147986 A1 | 7/2004 | Baumgardner et al. | |
| 2004/0199227 A1 | 10/2004 | Altshuler et al. | |
| 2005/0049228 A1 | 3/2005 | Albrecht et al. | |
| 2005/0055070 A1 | 3/2005 | Jones et al. | |
| 2005/0104059 A1 | 5/2005 | Friedman et al. | |
| 2005/0107849 A1 | 5/2005 | Altshuler et al. | |
| 2005/0107853 A1 | 5/2005 | Krespi et al. | |
| 2005/0207152 A1 | 9/2005 | Maxik | |
| 2005/0207159 A1 | 9/2005 | Maxik | |
| 2006/0030908 A1 | 2/2006 | Powell et al. | |
| 2006/0077672 A1 | 4/2006 | Schaak | |
| 2006/0085052 A1 | 4/2006 | Feuerstein et al. | |
| 2006/0262545 A1 | 11/2006 | Piepgras et al. | |
| 2007/0239143 A1 | 10/2007 | Altshuler et al. | |
| 2008/0008620 A1 | 1/2008 | Alexiadis | |
| 2008/0091250 A1 | 4/2008 | Powell | |
| 2008/0305004 A1 | 12/2008 | Anderson et al. | |
| 2009/0034236 A1 | 2/2009 | Reuben | |
| 2009/0076115 A1 | 3/2009 | Wharton et al. | |
| 2009/0199227 A1 | 8/2009 | Kennedy | |
| 2015/0182646 A1 | 7/2015 | Anderson et al. | |

FOREIGN PATENT DOCUMENTS

| | | |
|---|---|---|
| CN | 101272822 B | 12/2012 |
| EP | 0306301 A1 | 3/1989 |
| EP | 1495820 A1 | 1/2005 |
| EP | 1693016 A1 | 8/2006 |
| EP | 1924323 A1 | 5/2008 |
| EP | 1493820 B1 | 5/2013 |
| EP | 1887298 B2 | 2/2019 |
| FR | 2 773 715 A1 | 7/1999 |
| GB | 2442705 B | 11/2009 |
| JP | 10-156349 A | 6/1998 |
| JP | 2003-339845 A | 12/2003 |
| JP | 2004-261595 A | 9/2004 |
| JP | 2004-262595 A | 9/2004 |
| JP | 2004-275335 A | 10/2004 |
| JP | 2004-275927 A | 10/2004 |
| JP | 2007-511279 A | 5/2007 |
| JP | 05689580 B2 | 3/2015 |
| KR | 10-195941 B1 | 6/1999 |
| KR | 20-0357464 | 7/2004 |
| KR | 20-0371914 | 12/2004 |
| KR | 2008-052561 A | 6/2008 |
| KR | 2013-136597 A | 12/2013 |
| WO | WO 2001/014012 A1 | 3/2001 |
| WO | WO 2003/037504 A1 | 5/2003 |
| WO | WO 2003/063902 A1 | 8/2003 |
| WO | WO 2003/084601 | 10/2003 |
| WO | WO 2003/089063 | 10/2003 |
| WO | WO 2004/033028 A2 | 4/2004 |
| WO | WO 2005/048811 | 6/2005 |
| WO | WO 2005/049138 A1 | 6/2005 |
| WO | WO 2006/100303 A2 | 9/2006 |
| WO | WO 2006/126482 A1 | 11/2006 |
| WO | WO 2007/012875 A1 | 2/2007 |
| WO | WO 2009/056838 A1 | 5/2009 |

OTHER PUBLICATIONS

Almeida et al., "Porphyrins as Antimicrobial Photosensitizing Agents", Chapter 5 In Photodynamic Inactivation of Microbial Pathogens: Medical and Environmental Applications (Jun. 2011).

Ashkenazi, H., et al., "Eradication of Propionibacterium Acnes by its Endogenic Porphyrins after Illumination with High Intensity Blue Light", FEMS Immunology and Medical Microbiology, Jan. 2003, pp. 17-24, vol. 35, Elsevier Science B.V., The Netherlands.

Australian Government, IP Australia, Examiner's First Report for Application No. 2006273860, dated Jul. 16, 2010, 2 pages, Australia.

Australian Government, IP Australia, Examiner's Second Report for Application No. 2006273860, dated Oct. 19, 2011, 3 pages, Australia.

Australian Government, IP Australia, Notice of Acceptance for Application No. 2006273860, dated Apr. 10, 2012, 3 pages, Australia.

Bek-Thomsen, M., et al., "Acne is Not Associated with Yet-Uncultured Bacteria", J. Clin. Microbiol., Oct. 2008, pp. 3355-3360, vol. 46, No. 10, American Society for Microbiology, U.S.A.

Bisland et al., Pre-clinical in vitro and in vivo studies to examine the potential use of photodynamic therapy in the treatment of osteomyelitis, 5 Photochemical & Photobiological Sciences 31-38 (2006).

Bown et al., "The Biology of Photodynamic Therapy in the Gastrointestinal Tract," 10(3) Gastrointestinal Endoscopy Clinics of North America 533-550 (Jul. 2000).

Bridson, The Oxoid Manual, 8th Edition, pp. 2-178, 2-179, 3-6, 3-10, 3-14, 3-15, and 5-3, (1998).

Brochure for neoBlue LED Phototherapy, Natus Jaundice Management—neoBlue LED Phototherapy web archive dated Aug. 23, 2006.

Burkhart, C. N. and Gottwald, L., "Assessment of etiologic agents in acne pathogenesis," Skinned, 2003, vol. 2, No. 4, pp. 222-228.

Burkhart, C.G., et al., Acne: a review of immunologic and microbiologic factors, *Postgraduate Medical Journal*, 1999, vol. 75, pp. 328-331.

Caddick et al., "Molecular analysis of methicillin-resistant *Staphylococcus aureus* reveals an absence of plasmid DNA in multidrug-resistant isolates," FEMS Immunology and Medical Microbiology, 44:297-302, (2005).

Canadian Intellectual Property Office, Requisition by the Examiner for Application No. 2,617,205, dated Feb. 1, 2013, 3 pages, Canada.

Canadian Intellectual Property Office, Requisition by the Examiner for Application No. 2,617,205, dated Jan. 10, 2014, 3 pages, Canada.

Canadian Intellectual Property Office, Requisition by the Examiner for Application No. 2,617,205, dated Feb. 20, 2015, 4 pages, Canada.

Castano, et al., "Mechanisms in photodynamic therapy: part one—photosensitizers, photochemistry and cellular localization," Photodiagnosis Photodyn Ther. 1(4): 279-293, (Dec. 2004).

Chang et al., In vitro and in vivo photosensitizing capabilities of 5-ALA in vascular endothelial cells, 24(3) Lasers Surg Med. 178-186 (1999).

Choe et al., "Chemical Reactions and Stability of Riboflavin in Foods," Journal of Food Science, 70(1):R28-R36, (2005).

(56) References Cited

OTHER PUBLICATIONS

Clauditz, A., et al., "Staphyloxanthin plays a role in the fitness of *Staphylococcus aureus* and its ability to cope with oxidative stress," *Infection and Immunity*, 2006, vol. 74, No. 8, pp. 4950-4953.
Coia et al., Guidelines for the control and prevention of methicillin-resistant *Staphylococcus aureus* (MRSA) in healthcare facilities, Journal of Hospital Infection (Apr. 3, 2006).
Cree, Inc. Data Sheet entitled, G•Sic® Technology XBright™ Power chip LeED CXXX-XB900-X, 2001-2002.
Declaration and CV of Carrie Gardner dated Dec. 9, 2018.
Declaration and CV of Michael A. Sulzinski dated Dec. 9, 2018.
Declaration and CV of Raymond P. Goodrich, Ph.D. dated Apr. 15, 2019.
Declaration and CV of Zane Coleman dated Feb. 10, 2019.
Declaration Michael A. Sulzinski, in Support of Petitioner's Reply to Patent Owner's Response, dated Jan. 10, 2020.
Declaration of Brian J. Emfmger dated Dec. 10, 2018.
Demidova et al., "Photodynamic Therapy Targeted to Pathogens," Publication, 17(3):245.254, (2004).
Deposition of Dr. Michael A. Sulzinski, called by Patent Owner of U.S. Pat. No. 9,839,706 in Case IPR2019-00431, taken stenographically by Sandra L. Rocca, dated Sep. 13, 2019.
Deposition of Dr. Raymond P. Goodrich, taken by Petitioner, dated Dec. 20, 2019.
DeRosa et al., "Photosensitized single oxygen and its applications," Coordination Chemistry Reviews 233-234 (2002) 351-371.
Drews et al., Community-Associated Methicillin-Resistant *Staphylococcus aureus*: Review of an Emerging Public Health Concern, 105 Wise. Med. Journal 52 (Feb. 2006).
Elman et al., "The effective treatment of acne vulgaris by a high-intensity, narrow band 405-420 nm light source," J Cosmetic & Laser Ter. 5: 111-116, (2003).
European Patent Office, Brief Communication, Oral Proceedings on Mar. 1, 2016, for Application No. 06765156.2, Feb. 22, 2016, 5 pages, Germany.
European Patent Office, Communication pursuant to Article 94(3) EPC for Application No. 06765156.2, dated Aug. 4, 2010, 3 pages, Germany.
European Patent Office, Communication pursuant to Article 94(3) EPC for Application No. 06765156.2, dated Sep. 20, 2012, 4 pages, Germany.
European Patent Office, Communication pursuant to Article 94(3) EPC for Application No. 06765156.2, dated Feb. 3, 2014, 5 pages, Germany.
European Patent Office, Communication under Rule 71(3) EPC, Intention to Grant for Application No. 06765156.2, dated Mar. 21, 2016, 36 pages, Germany.
Excerpts from Chambers Science and Technology Dictionary, published jointly with W & R chambers Limited and the Press of the Syndicate of the Univ. of Cambridge, p. 520, Copyright 1988.
Excerpts from File History for U.S. Appl. No. 11/997,227, 393 pages.
Excerpts from File History for U.S. Appl. No. 14/657,398, 112 pages.
Excerpts from Handbook of Optics, Classical, vision & X-Ray Optics, Second Edition, vol. III, Chapter 7, pp. 7.1-7.12, and, Chapter 14, pp. 14.1-14.9, Copyright 2000.
Excerpts from Lighting Handbook, Reference & Application, 8th Edition, pp. 1-90, Copyright 1993.
Excerpts from McGraw-Hill Dictionary of Scientific and Technical Terms, McGraw-Hill 6th edition, pp. 189 and 390, ISBN: 0-07-042313-Xm, Copyright 2003.
Excerpts from McGraw-Hill Dictionary of Scientific and Technical Terms, McGraw-Hill 6th edition, p. 1588, Copyright 2004.
Excerpts from Merriam-Webster's Collegiate Dictionary, 11th Ed. (2003).
Excerpts from Organic Chemistry, vol. 1, 6th Ed. Organic Chemistry p. 901-902, Copyright 1973.
Excerpts from Stedman's Medical Dictionary, 27th Edition, pp. 523, 1697-1698, Copyright 2000.
Excerpts from Taber's Cyclopedic Medical Dictionary, 19th edition, p. 2040, Copyright 2001.
Figuerio, "Lighting the Way: A Key to Independence," Lighting Research Center, Copyright 2001 Rensselaer Polytechnic Institute.
Figure 4 of Ashkenazi et al., FEMS Immunology ad Medical Microbiology, 35:21, (2003), as Annotated by U.S. Pat. No. 9,839,70 Patent Owner and marked during deposition of Dr. Sulzinski on Sep. 13, 2019. [Submitted as Exhibit 2022 in IPR2019-00431/U.S. Pat. No. 9,839,706 Patent Owner's Response, entered Oct. 7, 2019].
Final Written Decision, IPR2019-00431, paper No. 38 (Jul. 8, 2020).
Ganz et al., "Helicobacter pylori in Patients Can Be Killed by Visible Light," Lasers Surg Med, 36(4): 260-265, (Apr. 2005).
GB Application No. 0515550.8 filed Jul. 29, 2005; Univ of Strathclyde.
GB Application No. 0721374.7 filed Oct. 31, 2007 Univ of Strathclyde.
Gold et al., "The use of a novel intense pulsed light and heat source and ALA-PDT in the treatment of moderate to severe inflammatory acne vulgaris," 3(6 Suppl) J Drugs Dermatol. S15-9 (Nov.-Dec. 2004).
Grzelak et al., "Light-Dependent Generation of Reactive Oxygen Species in Cell Culture Media," Publication,30(12):1418-1425, (2001).
Guffey et al., "Effects of Combined 405-nm and 880-nm Light on *Staphylococcus aureaus* and Psuedomonas aeruginosa in Vitro," Photomedicine and Laser Surgery, vol. 24, No. 6, 2006, pp. 680-683.
Guffey et al., "In Vitro Bactericidal Effects of 405-nm and 470-nm Blue Light," Photomedicine and Laser Surgery, vol. 24, No. 6, 2006, pp. 684-688.
Haddad et al., "Photodynamic therapy of murine colon cancer and melanoma using systemic aminolevulinic acid as a photosensitizer," 2(3) Int J Surg Investig. 171-178 English Abstract (2000).
Harrison, A.P., "Survival of Bacteria," *Annu. Rev. Microbiol.*, 1967, pp. 143-156, vol. 21.
Harth et al., "Modified topical photodynamic therapy of superficial skin tumors, utilizing aminolevulinic acid, penetration enhancers, red light, and hyperthermia," 24(7) Dermatol Surg. 723-726 (Jul. 1998).
Harth et al., Topical photodynamic therapy in basal and squamous cell carcinoma and penile Bowen's disease with 20% aminolevulinic acid, and exposure to red light and infrared light, 134(8) Harefuah 602-605, 672, 671, English Abstract, (Apr. 15, 1998).
International Commission on Illumination Technical Report entitled "CIE 1988 2° Spectral Luminous Efficiency Function of Photopic Vision," Oct. 2005.
International Searching Authority, Corrected International Search Report for Application No. PCT/GB2006/002841, dated Feb. 28, 2007, 5 pages, The Netherlands.
International Searching Authority, International Search Report and Written Opinion for International Application No. PCT/GB2006/002841, dated Nov. 17, 2006, 9 pages, The Netherlands.
IPR2019-00431 for U.S. Pat. No. 9,839,706 Petition of Inter Partes Review submitted Dec. 12, 2018.
IPR2019-00431/U.S. Pat. No. 9,839,706 Decision Institution of Inter Partes Review, entered Jul. 10, 2019.
IPR2019-00431/U.S. Pat. No. 9,839,706 Patent Owner's Preliminary Response submitted Apr. 15, 2019.
IPR2019-00431/U.S. Pat. No. 9,839,706 Patent Owner's Response, entered Oct. 7, 2019.
IPR2019-00431/U.S. Pat. No. 9,839,706 Petitioner's Reply to Patent Owner's Response, entered Jan. 10, 2020.
IPR2019-00431/U.S. Pat. No. 9,839,706 Petitioner's Updated Exhibit List, entered Jan. 4, 2019.
IPR2019-00588 for U.S. Pat. No. 9,039,966 Decision Denying Institution of Inter Partes Review, entered Sep. 30, 2019.
IPR2019-00588 for U.S. Pat. No. 9,039,966 Patent Owner's Preliminary Response, submitted Jul. 1, 2019.
IPR2019-00588 for U.S. Pat. No. 9,039,966 Petition of Inter Partes Review submitted Jan. 18, 2019.
IPR2019-00747 for U.S. Pat. No. 8,398,264 Decision Denying Institution of Inter Partes Review, entered Sep. 30, 2019.
IPR2019-00747 for U.S. Pat. No. 8,398,264 Patent Owner's Preliminary Response, submitted Jul. 1, 2019.

(56) References Cited

OTHER PUBLICATIONS

IPR2019-00747 for U.S. Pat. No. 8,398,264 Petition of Inter Partes Review submitted Feb. 27, 2019.
Japan Patent Office, Decision of Refusal for Application No. 2008-523460, drafted May 14, 2014, 10 pages, Japan.
Japan Patent Office, Decision to Grant a Patent Application No. 2008-523460, drafted Jan. 6, 2015, 6 pages, Japan.
Japan Patent Office, Notification of Reasons for Refusal for Application No. 2008-523460, drafted Aug. 13, 2013, 4 pages, Japan.
Japan Patent Office, Notification of Reasons for Refusal for Application No. 2008-523460, drafted Jul. 13, 2012, 6 pages, Japan.
Jappe, U., "Pathological mechanisms of acne with special emphasis on Proptonibacterium acnes and related therapy," *Acta Dermato-Venereologica*, 2003, vol. 83, pp. 241-248.
Kawada, Akira, et al., "Acne phototherapy with a high-intensity, enhanced, narrow-band, blue light source: an open study and in vitro investigation", Journal of Dermatological Science, Nov. 2002, pp. 129-135, vol. 30, No. 2, Elsevier Science Ireland Ltd., Ireland.
Kelty et al., The use of 5-aminolaevulinic acid as a photosensitiser in photodynamic therapy and photodiagnosis, 1 Photochem. Photobiol. Sci. 158-168 (2002).
Kim et al., Inactivation by 405±5 nm light emitting diode on *Escherichia coli* O157:H7, *Salmonella Typhimurium*, and Shigella sonnei under refrigerated condition might be due to the loss of membrane integrity, 59 Food Control 99-107 (Jan. 2016).
Kim et al., Photodynamic inactivation of *Salmonella enterica* Enteritidis by 405±5-nm light-emitting diode and its application to control salmonellosis on cooked chicken, 82 Food Control 305-315 (Dec. 2017).
Kim et al., Photodynamic Therapy induced Cell Death using ALA and 632nm Diode Laser in A549 Lung Cancer Cells, 56(2) Tuberc Respir Dis. 178-186 (Feb. 2004).
Kjeldstad et al., "Photoinactivation of Propionibacterium acnes by Near-Ultravioilet Light," Institute of Physics/NLHT, University of Trondheim, 39C, 300-302, (1984).
Kochevar et al., "Photosensitized Reactions of DNA: Cleavage and Addition," Bioorganic Photochemistry, Chapter 2, 1:275-315, ISBN: 0-471-62987-1, (1990).
Konig et al., "Red Light Kills Bacteria via Photodynamic Action," Cellular and Molecular Biology, 46(7), 1297-1303, (2000).
Korean Intellectual Property Office, Decision of Rejection for Amendment for Application No. 10-2008-7003589, dated Jan. 15, 2014, 4 pages, Republic for Korea.
Korean Intellectual Property Office, Notification of Final Rejection for Application No. 10-2008-7003589, dated Aug. 5, 2013, 4 pages, Republic for Korea.
Korean Intellectual Property Office, Notification of Final Rejection 10-2013-7032244, dated Aug. 20, 2014, 2 pages, Republic of Korea.
Korean Intellectual Property Office, Notification of Reason for Refusal for Application No. 10-2008-7003589, dated Oct. 16, 2012, 5 pages, Republic for Korea.
Korean Intellectual Property Office, Notification of Reason for Refusal 10-2013-7032244, dated Dec. 24, 2013, 5 pages, Republic of Korea.
Korean Intellectual Property Office, Notification of Result of Reexamination 10-2008-7003589, dated Jan. 15, 2014, 2 pages, Republic of Korea.
Maclean, "An Investigation into the Light Inactivation of Medically Important Microorganisms," Thesis presented for the degree of Doctor of Philosophy in Department of Electronic & Electrical Engineering, University of Strathclyde, (2006).
Mai et al., "The antibacterial effect of sinoporphyrin sodium photodynamic therapy on *Staphylococcus aureus* planktonic and biofilm culture," 48 Lasers in Surgery and Medicine 400-408 (2016).
Maier et al., Photosensitization with hematoporphyrin derivative compared to 5-aminolaevulinic acid for photodynamic therapy of esophageal carcinoma, 72(4) Ann Thorac Surg. 1136-1140 (Oct. 2001).
Marshall, J.H. and Wilmoth, G.J., "Pigments of *Staphylococcus aureus*, a series of trierpenoid carotenoids," *J. Bacteriology*. 1981, vol. 147, No. 3, pp. 900-913.
Moller et al., "How Finsen's light cured lupus vulgaris," Photodermatol Photoimmunol Photomed, 21: 118-124, (2005).
National Lighting Product Information Program Specifier Report entitled, "Specular Reflectors," vol. 1, Issue 3, Jul. 1992.
National Lighting Product Information Program Specifier Report entitled, "Screwbase Compact Fluorenscent Lamp Products," vol. 7, No. 1, Jun. 1999.
Nitzan et a., "Endogenous Porphyrin Production in Bacteria by δ-Aminolaevulinic Acid and Subsequent Bacterial Photoeradication," Lasers Med Sci, 14:269-277, (1999).
Nitzan et al., "ALA induced photodynamic effects on Gram positive and negative bacteria," Photochem. Photobiol. Sci., 3, 430-435, (2004).
Norlux Corporation Data Sheet entitled, "UV hex (40 Die) 395nm, 405nm, 414", Norlux Corporation, released Nov. 10, 2003.
Optek Technology Inc. Data Sheet entitled, "1-watt SMD 6mm (120° Viewing Angle)"—Issue A, Oct. 2006.
Optek Technology Inc. Data Sheet entitled, "1-watt SMD 6mm (120° Viewing Angle)"—Issue A.3, Oct. 2007.
Osnat Feuerstein, Nir Persman and Ervin I. Weiss, Phototoxic Effect of Visible Light on Porphyromonas gingivalis and Fusobacterium nucleatum: An In Vitro Study, Photochemistry and Photobiology, 2004, 80: 412-415, Dept. of Prosthodontics, Hebrew University-Hadassah School of Dental Medicine, Jerusalem, Israel.
Pelz, A. et al., "Structure and biosynthesis of staphyloxanthin from *Staphylococcus aureus*," *J.Bio. Chem.*, 2005, vol. 280, No. 37, pp. 32493-32498.
Philipp-Dormston et al., "Comparison of Porphyrin and Heme Biosyntesis in Various Heterotrophic Bacteria," Enzyme, 16: 57-64, (1973).
Pochi, P.E., Acne: Androgens and microbiology, *Drug Dev. Res.*, 1988, vol. 13, pp. 157-168.
Post-Institution Declaration of Raymond P. Goodrich, Ph.D., 60 pages, dated Oct. 7, 2019.
Sakai, K., et al., "Search for inhibitors of staphyloxanthin production by methicillin-resistant *Staphylcoccus aureus*," *Biol. Pharm. Bull*, 2012, vol. 35, No. 1, pp. 48-53.
Schubert et al., "Human eye sensitivity and photometric quantities," Light Emitting Diodes, 2nd Edition, Chapter 16, Copyright 2006.
Stenholm et al., "Methicillin-Resistant *Staphylococcus aureus* Screening by Online Immunometric Monitoring of Bacterial Growth under Selective Pressure," Antimicrobial Agents and Chemotherapy, 53(12):5088-5094, (2009).
The International Bureau of WIPO, International Preliminary Report on Patentability for International Application No. PCT/GB2006/002841, dated Jan. 29, 2008, 7 pages, Switzerland.
Tong, Y. and Lighthart, B., "Solar radiation is shown to select for pigmented bacteria in the ambient outdoor atmosphere," *Photochemistry and Photobiology*, 1997, vol. 65, No. 1, pp. 103-106.
Tong, Y., et al., "Population study of atmospheric bacteria at the Fengtai district of Beijing on two representative days," *Aerobiologia*, 1993, vol. 9, pp. 69-74.
Tsai et al., Comparative study on the ALA photodynamic effects of human glioma and meningioma cells, 24(4) Lasers in Surgery and Medicine 296-305 (Apr. 27, 1999).
U.S. Appl. No. 11/997,227, Interview Summary dated Jan. 7, 2011.
U.S. Appl. No. 12/729,802, Ex Parte Quayle Action mailed Aug. 13, 2012.
U.S. Appl. No. 12/729,802, Notice of Allowance dated Dec. 3, 2012.
UK Intellectual Property Office, Examination under Section 18(3) for Application No. 0617960.0, dated May 1, 2007, 2 pages, U.K.
UK Intellectual Property Office, Examination under Section 18(3) for Application No. 0617960.0, dated Feb. 14, 2008, 1 page, U.K.
UK Intellectual Property Office, Notification of Grant for Application No. 0617960.0, dated Oct. 13, 2009, 3 pages, U.K.
United States Patent and Trademark Office, Notice of Allowance and Fee(s) Due for U.S. Appl. No. 11/997,227, dated Feb. 12, 2015, 11 pages, U.S.A.

(56) References Cited

OTHER PUBLICATIONS

United States Patent and Trademark Office, Notice of Allowance and Fee(s) Due for U.S. Appl. No. 11/997,227, dated Mar. 2, 2015, 10 pages, U.S.A.
United States Patent and Trademark Office, Notice of Allowance and Fee(s) Due for U.S. Appl. No. 14/657,398, dated Oct. 5, 2017, 8 pages, U.S.A.
United States Patent and Trademark Office, Notice of Allowance and Fee(s) Due for U.S. Appl. No. 15/807,488, dated Nov. 18, 2020, 8 pages, U.S.A.
United States Patent and Trademark Office, Office Action for U.S. Appl. No. 11/997,227, dated Nov. 25, 2008, 7 pages, U.S.A.
United States Patent and Trademark Office, Office Action for U.S. Appl. No. 11/997,227, dated Sep. 14, 2009, 7 pages, U.S.A.
United States Patent and Trademark Office, Office Action for U.S. Appl. No. 11/997,227, dated Jan. 28, 2010, 7 pages, U.S.A.
United States Patent and Trademark Office, Office Action for U.S. Appl. No. 11/997,227, dated Jul. 19, 2010, 9 pages, U.S.A.
United States Patent and Trademark Office, Office Action for U.S. Appl. No. 11/997,227, dated Mar. 7, 2011, 10 pages, U.S.A.
United States Patent and Trademark Office, Office Action for U.S. Appl. No. 11/997,227, dated Aug. 25, 2011, 8 pages, U.S.A.
United States Patent and Trademark Office, Office Action for U.S. Appl. No. 11/997,227, dated Sep. 12, 2012, 7 pages, U.S.A.
United States Patent and Trademark Office, Office Action for U.S. Appl. No. 11/997,227, dated Jun. 20, 2013, 10 pages, U.S.A.
United States Patent and Trademark Office, Office Action for U.S. Appl. No. 11/997,227, dated Dec. 4, 2013, 15 pages, U.S.A.
United States Patent and Trademark Office, Office Action for U.S. Appl. No. 11/997,227, dated Apr. 25, 2014, 11 pages, U.S.A.
United States Patent and Trademark Office, Office Action for U.S. Appl. No. 14/657,398, dated Aug. 10, 2016, 16 pages, U.S.A.
United States Patent and Trademark Office, Office Action for U.S. Appl. No. 14/657,398, dated Apr. 4, 2017, 11 pages, U.S.A.
United States Patent and Trademark Office, Office Action for U.S. Appl. No. 15/807,488, dated Apr. 30, 2020, 8 pages, U.S.A.
U.S. Appl. No. 11/997,227 Amendment After Final dated Jun. 30, 2014.
Wielders et al., "mecA Gene Is Widely Disseminated in *Staphylococcus aureus* Population," Journal of Clinical Microbiology, 40(11):3970-3975, (2002).
Zuccarelli et al., "Diversity and Stability of Restriction Enzyme Profiles of Plasmid DNA from Methicillin-Resistant *Staphylococcus aureus*," Journal of Clinical Microbiology, 28(1):97-102, (1990).
U.S. Appl. No. 15/807,488, filed Nov. 8, 2017, U.S. Pat. No. 10,953,117, Patented.
U.S. Appl. No. 14/657,398, filed Mar. 13, 2015, U.S. Pat. No. 9,839,706, Patented.
U.S. Appl. No. 11/997,227, filed Jul. 3, 2008, U.S. Pat. No. 9,039,966, Patented.
University of Strathclyde V. Clear-Vu Lighting LLC, 2020-2243 (Fed. Cir. Nov. 4, 2021), Appeal from the U.S. Patent and Trademark Office, PTAB No. IPR2019-00431, Decision reversing PTAB's obviousness determination, 19 pages.

INACTIVATION OF GRAM-POSITIVE BACTERIA

CROSS-REFERENCE TO RELATED APPLICATIONS

This application is a continuation of U.S. application Ser. No. 15/807,488 filed Nov. 8, 2017, which is a continuation of U.S. application Ser. No. 14/657,398, filed Mar. 13, 2015, now U.S. Pat. No. 9,839,706, which is a continuation of U.S. application Ser. No. 11/997,227, filed Jul. 3, 2008, now U.S. Pat. No. 9,039,966, filed May 26, 2015, which is a U.S. National Stage of International Application No. PCT/GB2006/002841, filed Jul. 28, 2006, which claims the benefit of Great Britain Application No. 0515550.2, filed Jul. 29, 2005, the contents of which are hereby incorporated herein in their entirety by reference.

The present invention relates to a method for inactivating medically important Gram-positive bacteria including *Staphylococcus aureus* and methicillin (multi)-resistant *Staphylococcus aureus* (MRSA), Coagulase-Negative *Staphylococcus* (CONS), *Streptococcus*, *Enterococcus* and *Clostridium* species.

BACKGROUND OF THE INVENTION

Methicillin-resistant *Staphylococcus aureus* (MRSA) is becoming an increasingly problematic micro-organism, with infection rates rising and effective methods of control becoming more and more limited. In addition to the resistance of MRSA to antibiotics, there is a significant problem due to the availability of few effective sterilisation methods for environmental decontamination; for example in air and on contact surfaces. Public and media interest in the transmission and control of MRSA is escalating and it is becoming one of the most significant problems within the healthcare industry. Hospitals and nursing homes are the worst affected areas. Furthermore, community-acquired MRSA is also now being recognised as an increasing problem, with transmission occurring in public and social areas such as public gyms and sports centres.

As well as MRSA, other Gram-positive bacteria are known to cause health problems, particularly in the hospital environment. For example, *Staphylococcus epidermidis*, which is a Coagulase-Negative *Staphylococcus* (CONS), can cause infection, particularly in infants and in hospitalised patients who have received prosthetic implant surgery. *Streptococcus pyogenes* is a Gram-positive coccus commonly associated with infections such as pharyngitis, pyoderma, scarlet fever, erysipelas, cellulitis, streptococcal toxic-shock syndrome, rheumatic fever, glomerulonephritis, bacteraemia and necrotizing fasciitis, often referred to as "flesh-eating bacteria". *Enterococcus faecalis* (another Gram-positive coccus) is a common cause of urinary tract and wound infections, as well as other infections including bacteraemia, endocarditis and meningitis in severely ill hospitalised patients. Multi-antibiotic resistance is also becoming a well-documented problem with enterococcal infections. *Clostridium* species, in particular *C. difficile*, have been associated with high mortality in elderly patients due to diarrohea-associated dehydration, medically known as antibiotic-associated pseudomembranous colitis.

Many techniques have been proposed for destroying harmful bacteria, such as MRSA. For example, U.S. Pat. No. 6,251,127 describes a photodynamic process for the inactivation of bacteria and fungal wound infections using methylene blue or toluidene blue. Light energy in combination with photosensitising agents is used to treat or detect pathologies of living tissue, including cancer and microbiological pathogens. The light used has wavelengths ranging from about 450 nm to about 850 nm. Tests demonstrate the efficacy of the light treatment in combination with the photosensitising agents for the destruction of *Staphylococcus aureus* in in-vivo infected wounds; and for in-vitro destruction of antibiotic-resistant *Staphylococcus*, *Streptococcus*, *Enterococcus*, *E. coli*, *Pseudomonas*, *Haemophilus influenza* and *Candida albicans*. In addition, wavelength spectra of activation of methylene blue and toluidine blue in the presence of various concentrations of the above bacteria and *Candida* have been provided.

Whilst in some environments, the methodology of U.S. Pat. No. 6,251,127 may be useful, it nevertheless suffers from the significant practical disadvantage that photosensitising agents must be applied to the bacteria that are to be inactivated. A similar problem arises with US2005/0049228, which also requires the combined use of a photosensitiser and light; in this case, in the range of 500 nm to 580 nm. The need for photosensitising agents is a significant limitation of these techniques.

An objective of the present invention is to provide a simple and effective technique for inactivating selected bacteria, in particular MRSA, and more generally the *Staphylococcus*, *Streptococcus*, *Enterococcus* and *Clostridium* species.

SUMMARY OF THE INVENTION

A method for inactivating one or more pathogenic gram-positive bacterial comprising exposure of the bacteria to visible light without using a photosensitiser.

Preferably said bacteria are selected from *Staphylococcus*, in particular MRSA, CONS, *Streptococcus*, *Enterococcus* and *Clostridium* species.

It is understood that the term pathogenic is used in the context of gram-positive bacterial species and/or strains, which are capable of causing disease or infection in a human or animal subject. It is also understood that some bacteria are often commensal in that they are able to colonise and/or live on/within a healthy host and not become pathogenic unless or until the host becomes immunocompromised and/or unhealthy due to some other form of disease or injury, such as a wound. Such "potentially" pathogenic bacteria are encompassed by the invention also.

Moreover, the term inactivation is understood to mean that said bacteria are killed, or damaged so as to reduce or inhibit bacterial replication. The methods and systems taught herein can therefore be considered as bactericidal and/or bacteriostatic and this may depend on the species/strain of bacteria, wavelength of light, dose, etc.

Exposing these bacteria to blue light, or white light containing blue light, has been found to stimulate an inactivation process. An advantage of using light in the visible-wavelength region is that there is no detrimental effect on human or animal health. Consequently, the method can be used for an extensive range of applications, such as air disinfection, contact-surface and materials disinfection and, most noteworthy, wound protection and tissue disinfection.

According to another aspect of the invention, there is provided a method for inactivating pathogenic gram positive bacteria including at least one of Methicillin-resistant *Staphylococcus aureus* (MRSA), Coagulase-Negative *Staphylococcus* (CONS), *Streptococcus*, *Enterococcus* and *Clostridium* species comprising exposure of the bacteria to visible light having a wavelength in the range 400-500 nm.

The visible light may have a wavelength in the range 400-450 nm. The light may have a wavelength in the range 400-420 nm. The light may have a wavelength of 405 nm.

According to yet another aspect of the invention, there is provided a system for inactivating pathogenic Gram-positive bacteria including Methicillin-resistant *Staphylococcus aureus* (MRSA), Coagulase-Negative *Staphylococcus* (CONS), *Streptococcus, Enterococcus* and *Clostridium* species, comprising the means for exposing them to visible light having a wavelength in the range of 400-500 nm. The wavelength of the light used is preferably in the range 400-500 nm. The wavelength may be in the range 400-450 nm, and more specifically in the range 400-420 nm, with optimal inactivation at 405 nm.

According to still another aspect of the invention, there is provided use of visible light having a wavelength in the range of 400-500 nm, especially 400-420 nm for inactivating pathogenic gram positive bacteria including at least one of Methicillin-resistant *Staphylococcus aureus* (MRSA), Coagulase-Negative *Staphylococcus* (CONS), *Streptococcus, Enterococcus* and *Clostridium* species.

BRIEF DESCRIPTION OF THE DRAWINGS

Various aspects of the present invention will now be described by way of example only and with reference to the accompanying drawings, of which.

DETAILED DESCRIPTION OF THE DRAWINGS

Figure 1:
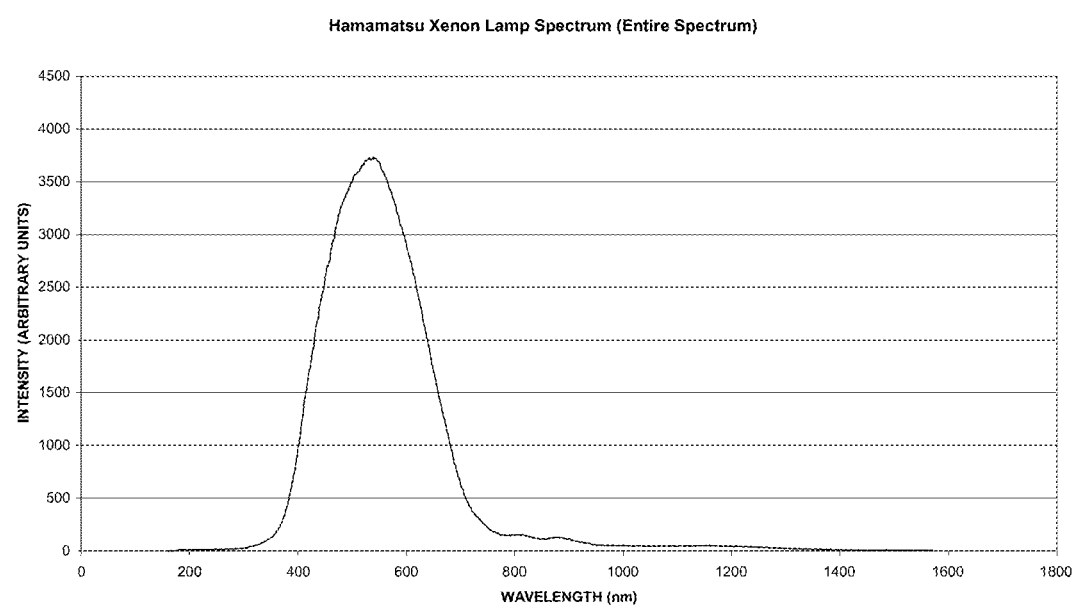
FIG. 1 shows the total emission spectrum of a Hamamatsu Xenon lamp.
Figure 2:
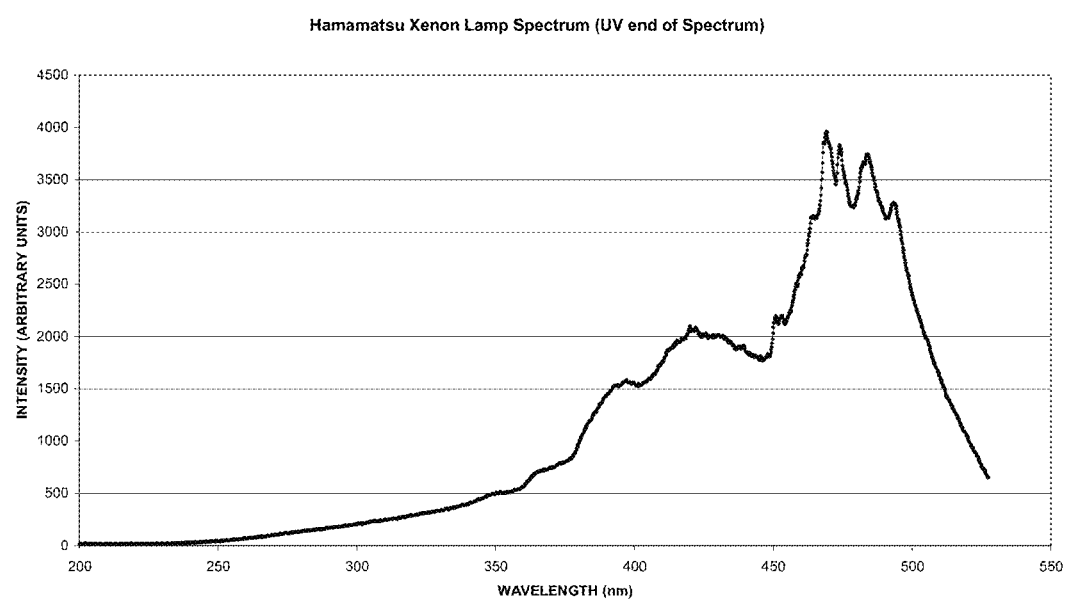
FIG. 2 shows in greater detail the ultra-violet emission spectrum of the Xenon lamp of FIG. 1.

Exposing MRSA to blue light has been found to cause significant inactivation. This narrow range of wavelength is part of the white-light spectrum. For all white-light sources, only a small fraction of the light output is in this range, typically one or two percent. Hence, to provide a sufficient amount of light and demonstrate the effectiveness of this technique, the source used was a Xenon lamp (Hamamatsu Photonics UK Limited). Emission spectra of the lamp are shown in FIGS. 1 and 2. The lamp was used in combination with an optical-fibre light guide and a selection of optical filters in order to allow exposure of the *Staphylococcus aureus* suspensions to specified wavelengths of visible light. The output of the light guide was maintained at a distance of 5 cm from the sample during all experiments.

To demonstrate the effectiveness of the technique, various studies have been carried out. The bacteria used were as follows: *Staphylococcus aureus* NCTC 4135; methicillin-resistant *Staphylococcus aureus* LMG 15975; methicillin-resistant *Staphylococcus aureus* 16a (clinical isolate), *Staphylococcus epidermidis* NCTC 7944, *Streptococcus pyogenes* NCTC 8198 *Enterococcus* faecali and *Clostridium perfringens* 13124. Each sample was serially diluted to the appropriate concentration using phosphate-buffered saline (PBS), plated out using nutrient agar (NA) and then incubated at 37° C. for 24 hours.

Figure 3:
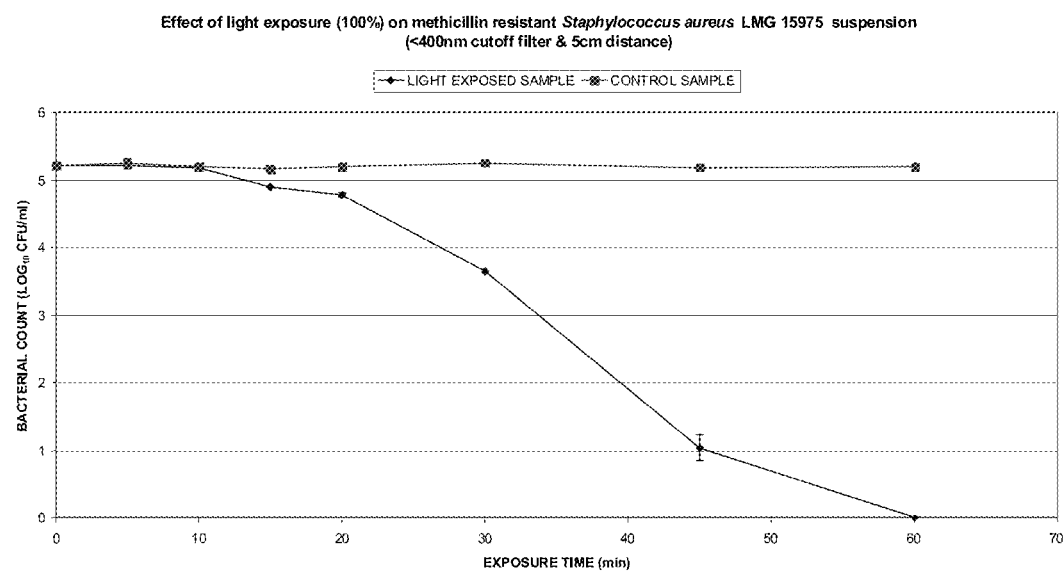
FIG. 3 is a plot of bacterial count of a methicillin-resistant *S. aureus* strain as a function of time of exposure to light of wavelength greater than 400 nm.
Figure 4:
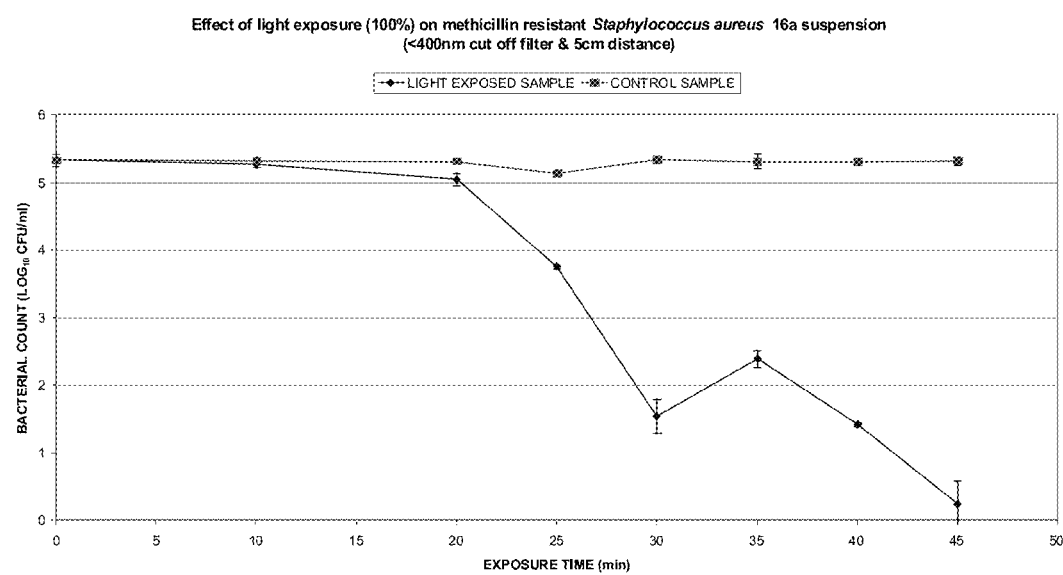
FIG. 4 is a plot of bacterial count of a second methicillin-resistant *S. aureus* strain as a function of time of exposure to light of wavelength greater than 400 nm.

Suspensions of methicillin-resistant *Staphylococcus aureus* LMG 15975 and clinical isolate 16a were prepared and exposed to visible light. The light was transmitted through a 400 nm long-wave pass filter (50% cut-off in transmission at 400 nm) before impacting on the bacterial suspension. This allowed only wavelengths of 400 nm and above (visible light) to illuminate the sample. The results of these experiments are shown in FIGS. 3 and 4. From these, it can be seen that the light treatment causes significant reduction in the counts of both the culture collection MRSA (LMG 15975) and the highly resistant clinical isolate (16a). The control data refer to samples that were untreated over the same time interval.

Figure 5:
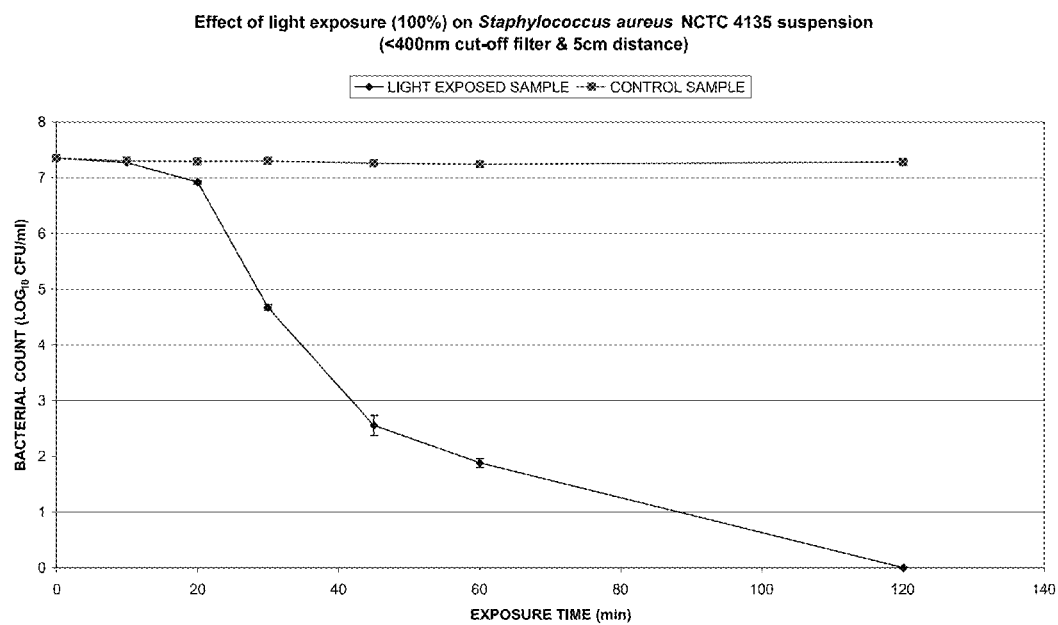
FIG. 5 is a plot of bacterial count of *S. aureus* NCTC 4135 as a function of time of exposure to light of wavelength greater than 400 nm.
Figure 6:
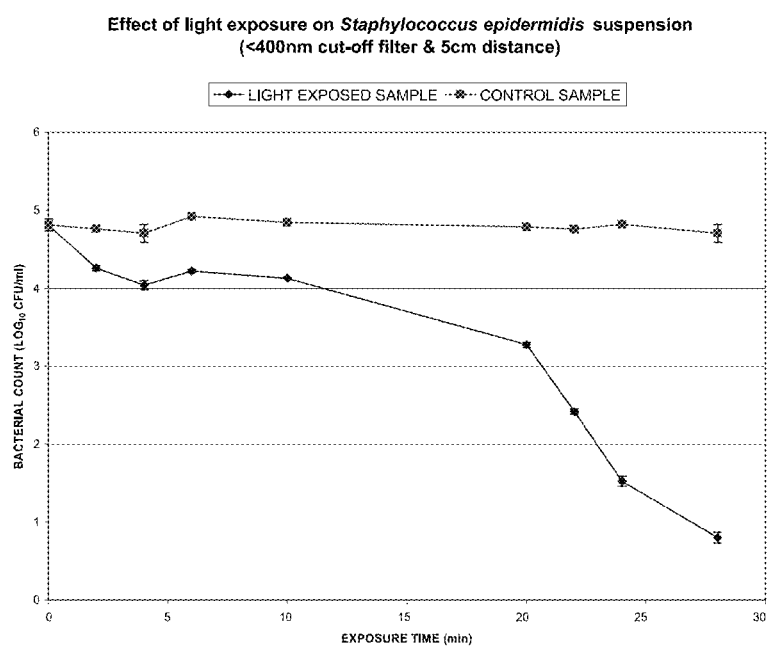
FIG. 6 is a plot of bacterial count of *S. epidermidis* NCTC 7944 as a function of time of exposure to light of wavelength greater than 400 nm.
Figure 7:
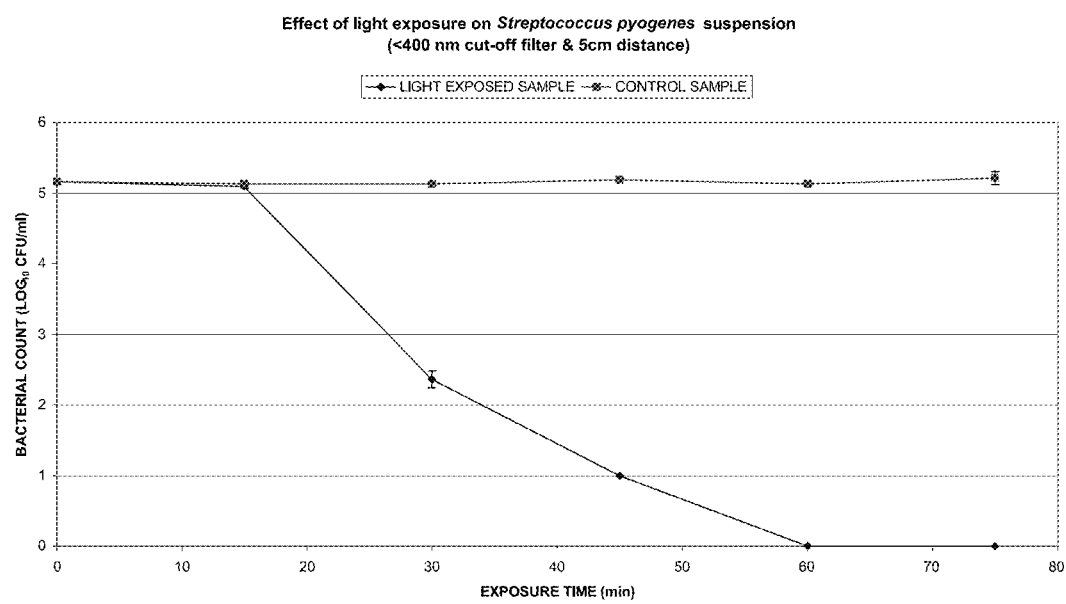
FIG. 7 is a plot of bacterial count of *Streptococcus pyogenes* NCTC 8198 as a function of time of exposure to light of wavelength greater than 400 nm.
Figure 8:
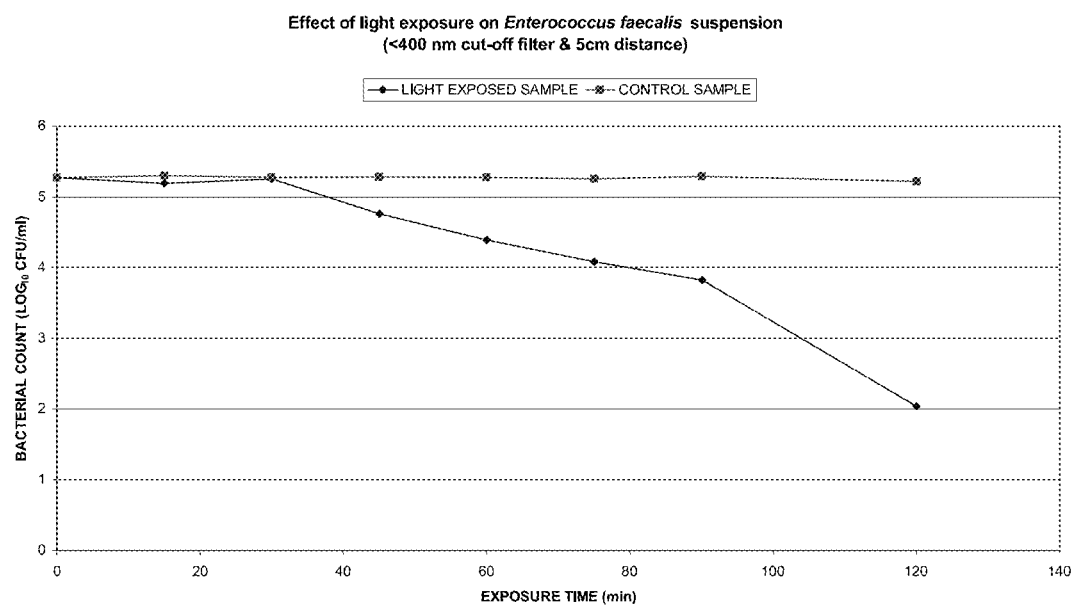
FIG. 8 is a plot of bacterial count of *Enterococcus faecalis* as a function of time of exposure to light of wavelength greater than 400 nm.

Suspensions of *Staphylococcus aureus* NCTC 4135 were also exposed to visible-light treatment. Again, the light beam was transmitted through a 400 nm long-wave pass filter before impacting on the bacterial suspension, allowing only the transmission of wavelengths of 400 nm and above. From FIG. 5 it can be seen that the Xenon light source caused significant reduction in the *Staphylococcus aureus* count even with a high starting bacterial population of approximately 10 colony-forming units per millilitre (cfu/ml). Similar experiments were carried out using *Staphylococcus epidermidis* NCTC 7944, *Streptococcus pyogenes* NCTC 8198 and *Enterococcus faecalis*. The associated reductions in the bacterial population are shown in FIGS. 6, 7 and 8. In each of these a significant reduction in the bacterial count is observed.

Figure 9:
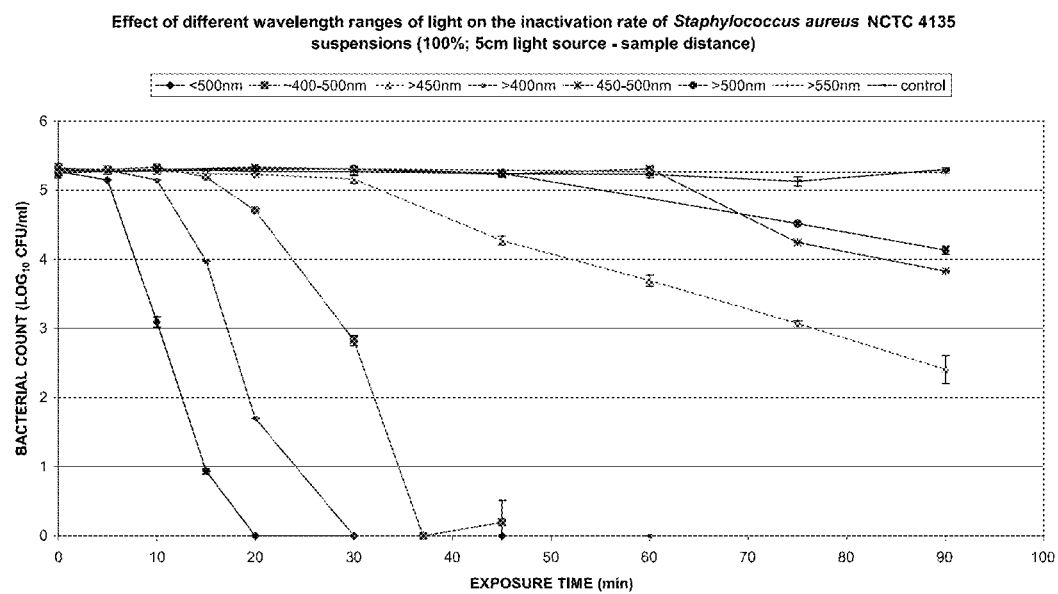
FIG. 9 is plots of bacterial count in a suspension of *S. aureus* NCTC 4135 as a function of time of exposure to light for different wavelength ranges.

Exposure tests using a range of filters were carried out. Bacterial suspensions were exposed to the following wavelength ranges for times up to 90 minutes: greater than 550 nm (using a 550 nm long-wave pass filter); greater than 500 nm (using a 500 nm long-wave pass filter), less than 500 nm (using a 500 nm short-wave pass filter); 400-500 nm (using a 400 nm long-wave pass filter and a 500 nm short-wave pass filter in combination); 450-500 nm (using a 450 nm long-wave pass filter and a 500 nm short-wave pass filter in combination); greater than 450 nm (using a 450 nm long-wave pass filter), and greater than 400 nm (using a 400 nm long-wave pass filter). The resultant inactivation curves in FIG. 9 allow only qualitative comparisons to be made since the filters do not have sharp cut-off wavelengths and the light intensities falling on the suspensions were different for the different curves. The results do however indicate that the wavelength region between 400 nm and 500 nm does provide a high rate of S. aureus inactivation.

Experiments were also carried out using bandpass filters each with a 10 nm FWHM (full-width, half-maximum). Suspensions of methicillin-resistant S. aureus LMG 15975 (approximately 105 cfu/ml population) were exposed to visible light transmitted through the following bandpass filters: 400 nm, 405 nm, 410 nm, 415 nm, 420 nm, 430 nm, 440 nm, and 450 nm. The intensity of the lamp was altered for each filter to ensure that the light power at the suspension was the same for each measurement, thus allowing direct comparison of results. The results of these experiments showed that samples exposed using the 400 nm, 405 nm and 415 nm bandpass filters have a reduced colony-forming-unit count/ml; that is, light of wavelengths within these narrow bandwidths had an inactivating effect on the S. aureus strains.

Figure 10:
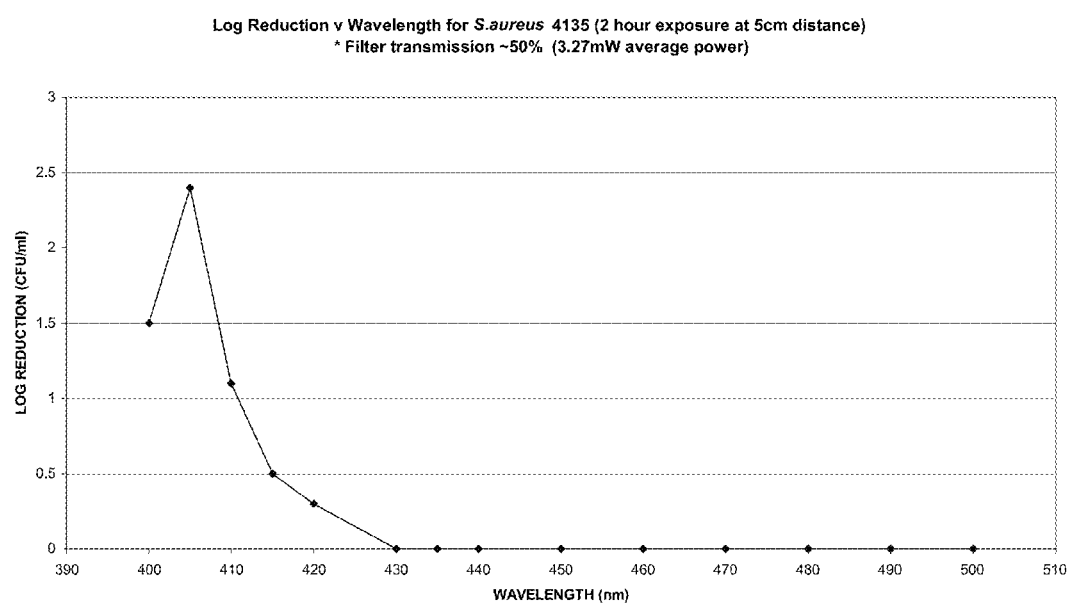
FIG. 10 is a plot of bacterial log reduction as a function of wavelength (400-500 nm) for *S. aureus* NCTC 4135.

A more detailed analysis of wavelength sensitivity was performed using suspensions of S. aureus NCTC 4135, and this is shown in FIG. 10. The results show that samples exposed using the 400 nm, 405 nm, 410 nm, 415 nm and 420 nm bandpass filters have a reduced colony-forming-unit count/ml; that is, light of wavelengths within these narrow bandwidths had an inactivating effect on the S. aureus strains. From these results it can be deduced that visible-light exposure over the wavelength range 400-450 nm is the major inducing factor for Staphylococcal inactivation, with increased inactivation occurring over the range 400-420 nm and optimum inactivation occurring at 405 nm. Moreover, it has been observed that a lower dose is required at this wavelength and typically the dose is less than 200 J/cm$^2$, such as less than 100 J/cm$^2$.

Figure 11:
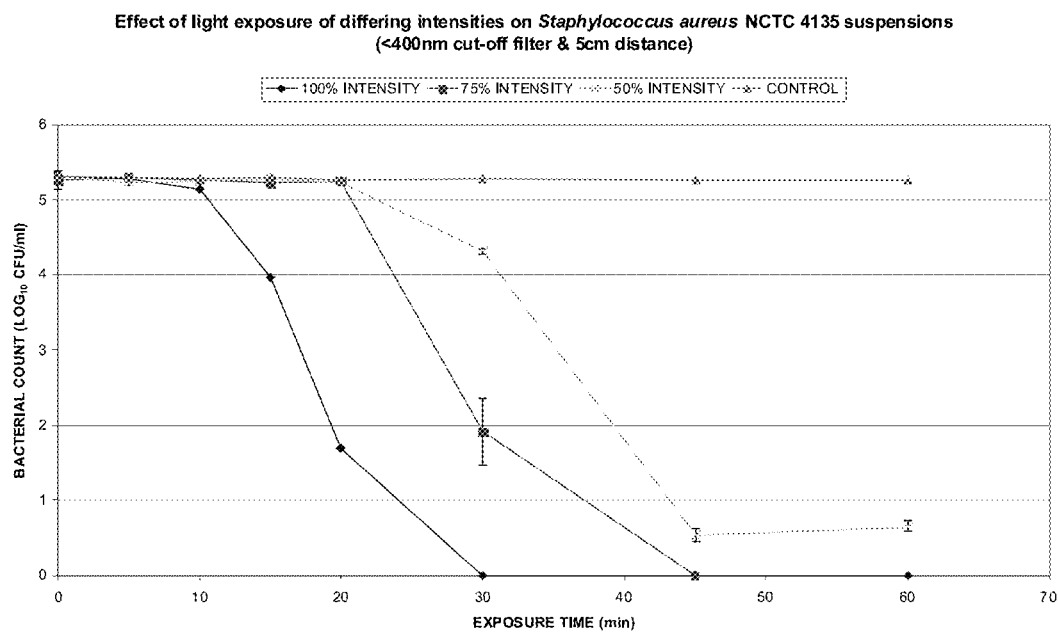
FIG. 11 is plots of bacterial count in a suspension of *S. aureus* NCTC 4135 as a function of time of exposure to light of wavelength greater than 400 nm for different light intensities.

In further experiments, Staphylococcus aureus NCTC 4135 suspensions were exposed to different intensities of visible-light treatment. These measurements were made using the 400 nm long-wave pass filter, that is, for wavelengths greater than 400 nm. FIG. 11 shows the results of these experiments. It can be seen that as the intensity of the light decreases, so to does the inactivation rate. The specific doses required for complete inactivation of Staphylococcal, Streptococcal and Enterococcal species using different filters and light intensities were determined. Sample results are shown in the Table below:

| ORGANISM | WAVELENGTH RANGE | DOSE (J/cm$^2$) | J/cm$^2$/log reduction |
|---|---|---|---|
| S. aureus 4135 | >400 nm (100% intensity) | 630 | 126 |
| S. aureus 4135 | >400 nm (75% intensity) | 729 | 145.8 |
| S. aureus 4135 | >400 nm (50% intensity) | 648 | 144 |
| S. aureus 4135 | <500 nm | 189.6 | 37.92 |
| S. aureus 4135 | 400-500 nm | 290.8 | 58.2 |
| MRSA 15975 | >400 nm | 1260 | 252 |
| MRSA 16a | >400 nm | 945 | 189 |
| S. epidermidis NCTC 7944 | >400 nm | 840 | 168 |
| Strep. pyogenes NCTC 8198 | >400 nm | 1440 | 288 |
| E. faecalis | >400 nm | 2880 | 1440 |

Figure 12:
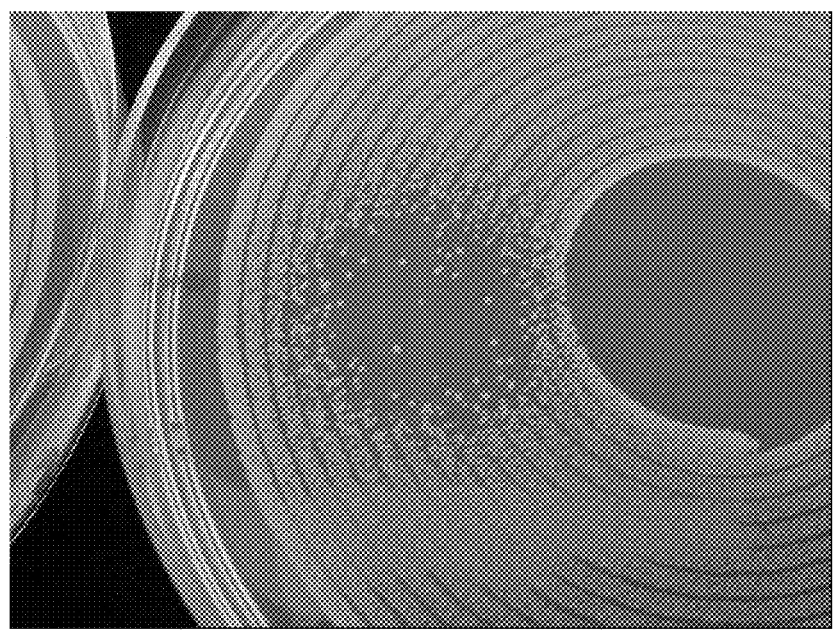
FIG. 12 is a visual indication of the surface inactivation of *S. aureus* NCTC 4135 through exposure to light of wavelengths greater than 400 nm. Surface inactivation is evidenced by inhibition of *S. aureus* growth on the areas exposed to this light.
Figure 13:
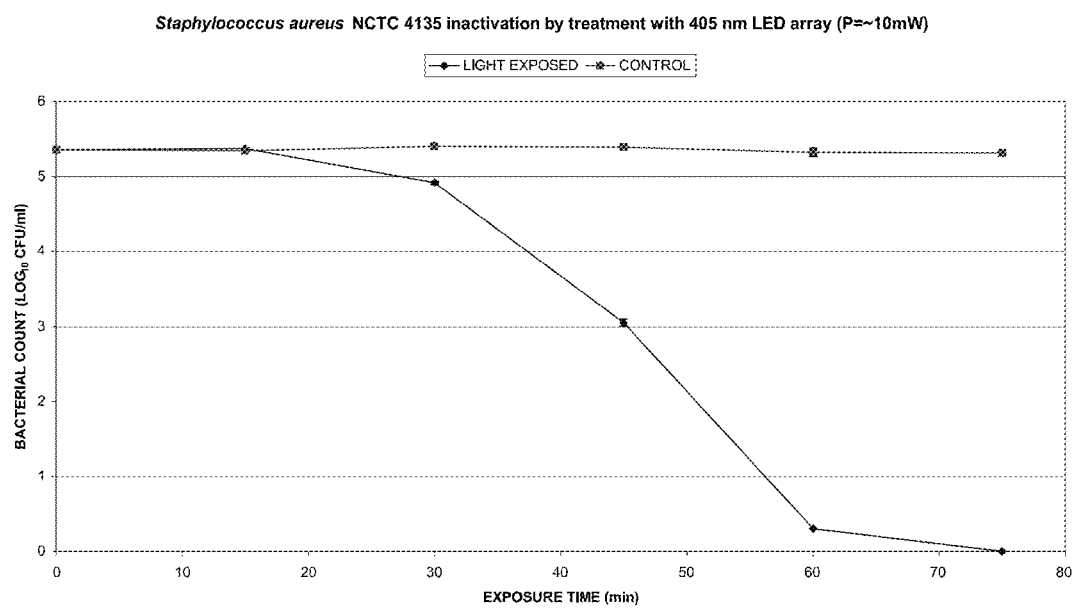
FIG. 13 is a plot of bacterial count of *S. aureus* NCTC 4135 as a function of time of exposure to light of 405 nm.
Figure 14:
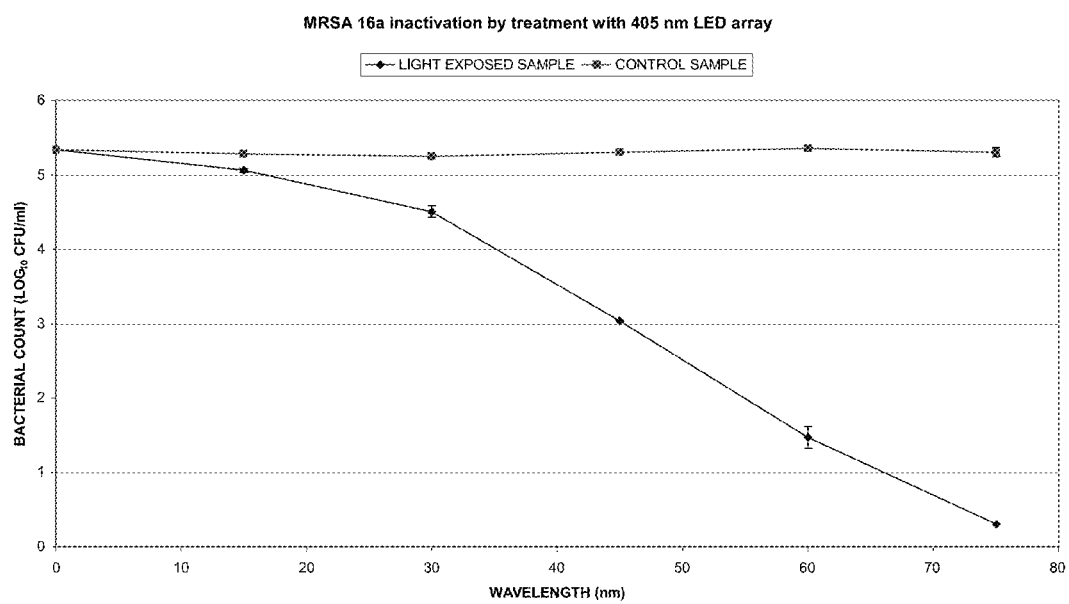
FIG. 14 is a plot of bacterial count of a methicillin-resistant *S. aureus* strain as a function of time of exposure to light of 405 nm.
Figure 15:
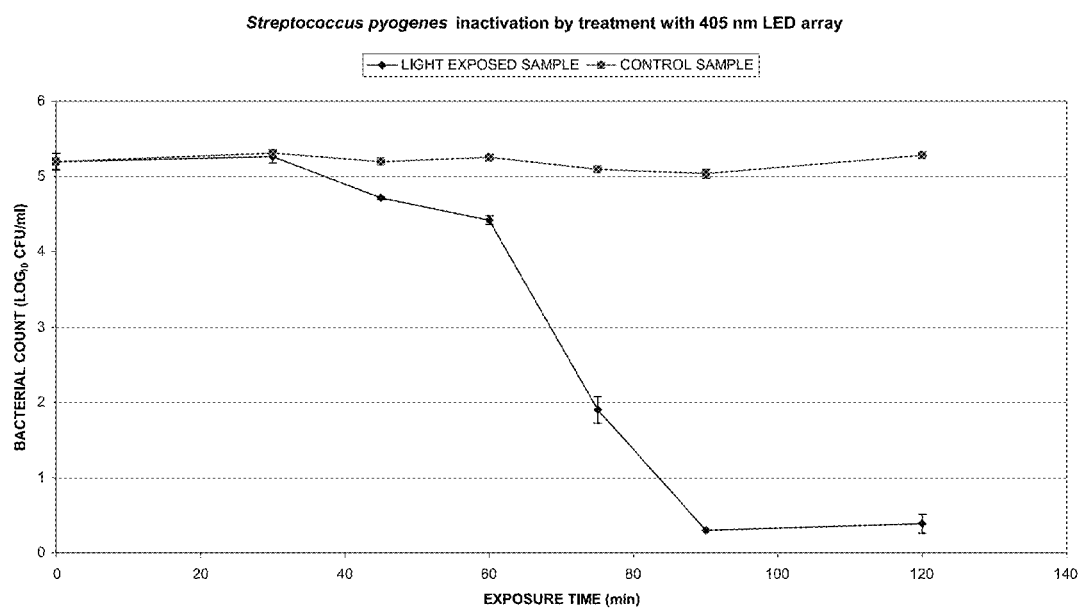
FIG. 15 is a plot of bacterial count of *Streptococcus pyogenes* NCTC 8198 as a function of time of exposure to light of 405 nm.
Figure 16:
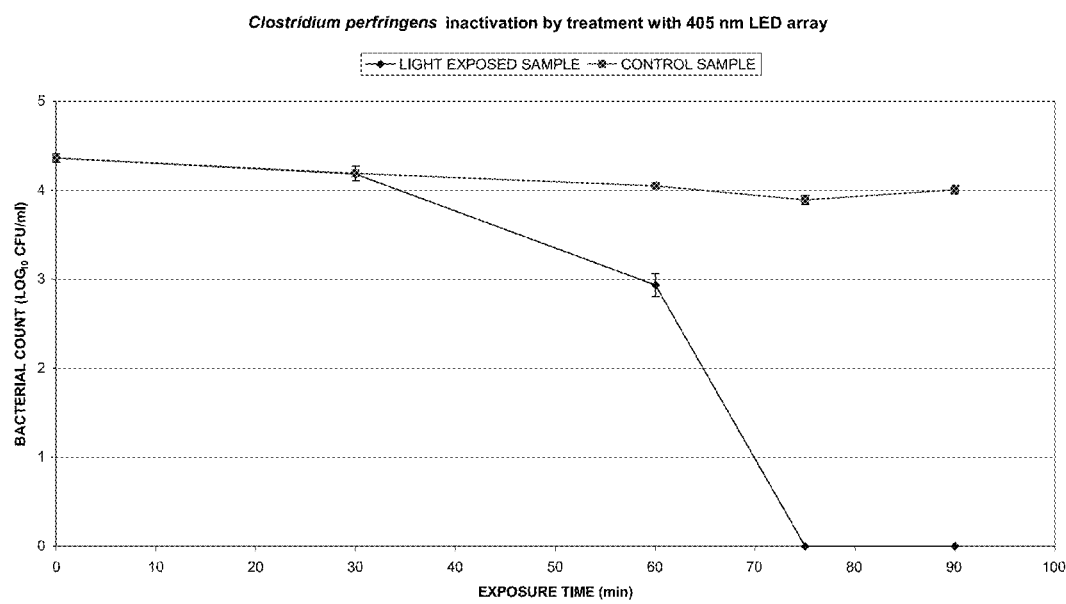
FIG. 16 is a plot of bacterial count of *Clostridium perfringens* 13124 as a function of time of exposure to light of 405 nm.

The effect of visible-light exposure for surface decontamination was also examined. This was done by exposing S. aureus cells, which were plated onto nutrient agar, to the light treatment (through a 400 nm long-wave pass filter) prior to incubation. Examples of results are shown as the areas of growth inhibition on the culture plates in FIG. 12.

A similar treatment system to that used with the Xenon lamp was assembled using a 405 nm LED array as a light source. Experiments were carried out using Staphylococcus aureus NCTC 4135, MRSA 16a, Streptococcus pyogenes NCTC 8198 and Clostridium perfringens 13124. The associated reductions in the bacterial population are shown in FIGS. 13, 14, 15 and 16, respectively. The specific doses required for complete inactivation of Staphylococcus, Streptococcus and Clostridium species using the 405 nm LED array were determined. Sample results are shown in the Table below:

| ORGANISM | WAVELENGTH | DOSE (J/cm$^2$) | J/cm$^2$/log reduction |
|---|---|---|---|
| S. aureus 4135 | 405 nm | 36 | 7.2 |
| MRSA 16a | 405 nm | 45 | 9 |
| Streptococcus pyogenes NCTC 8198 | 405 nm | 54 | 10.8 |
| Clostridium perfringens 13124 | 405 nm | 45 | 10.2 |

A comparison of the doses required for bacterial inactivation (5-log reduction) using light of wavelengths greater than 400 nm from the Xenon lamp and a 405 nm LED array is shown in the Table below:

| | DOSE (J/cm$^2$) | | J/cm$^2$/log reduction | |
|---|---|---|---|---|
| ORGANISM | >400 nm | 405 nm | >400 nm | 405 nm |
| S. aureus NCTC 4135 | 630 | 36 | 126 | 7.2 |
| MRSA 16a | 945 | 45 | 189 | 9 |
| Cl. perfringens 13124 | 1440 | 54 | 288 | 10.8 |

The use of 400-500 nm, in particular 400-450 nm, wavelengths of visible light (blue light) has proved to be an effective means of inactivation of Staphylococcus strains, including MRSA, as well as CONS, Streptococcus, Enterococcus and Clostridium, with increased inhibition rates in the 400-420 nm range and in particular, around 405 nm. This demonstrates that a light source (continuous source, flashlamp, laser etc.) with output at wavelengths in these regions could potentially be used in clinical environments for the reduction in levels of methicillin-resistant Staphylococcus aureus, and other medically important Gram-positive species; present in the air and on contact surfaces and materials, and most importantly, could be used for wound protection and tissue treatment. The exact parameters required would depend on the bacterial strain, the wavelength of the light being used and the light intensity. These can be readily determined experimentally.

Variations of the disclosed arrangements are possible without departing from the invention. For example, although both a Xenon lamp with a variety of different filters and a 405 nm LED array have been used as the inactivation source, it will be appreciated that any suitable light source can be used. Equally, although a particular experimental arrangement has been described here, it will be readily apparent that the light source used could be included in, for example, a hand-held device or could be designed to operate in or around areas that have to be kept free of MRSA. Accordingly the above description of the specific embodiment is made by way of example only and not for the purposes of limitation. It is clear that minor modifications may be made without significant changes to the operation described.

The invention claimed is:

1. A method for disinfecting air, contact surfaces, or materials by inactivating bacteria from one or more pathogenic Gram-positive bacterial species in the air, on the contact surfaces, or on the materials, said method comprising exposing the one or more pathogenic Gram-positive bacterial species to white light containing blue light without using a photosensitizer, wherein the one or more pathogenic Gram-positive bacterial species comprise *Enterococcus* species, wherein at least a portion of the blue light that inactivates the one or more Gram-positive bacterial species consists of wavelengths in the range of 400-500 nm, and wherein the method is performed outside the human body, and the contact surfaces or the materials are non-living.

2. The method of claim 1, wherein the portion of the blue light that inactivates the one or more Gram-positive bacterial species consists of wavelengths in the range 400-450 nm.

3. The method of claim 1, wherein the portion of the blue light that inactivates the one or more Gram-positive bacterial species consists of wavelengths in the range 400-420 nm.

4. The method of claim 1, wherein the portion of the blue light that inactivates the one or more Gram-positive bacterial species has a wavelength of about 405 nm.

5. The method of claim 4, wherein the portion of blue light that inactivates the one or more Gram-positive bacterial species is supplied from a light source comprising an LED.

6. The method of claim 1, wherein the portion of blue light that inactivates the one or more Gram-positive bacterial species is supplied from a light source comprising an LED.

7. The method of claim 6, wherein the light source is an LED array.

* * * * *